(12) United States Patent
Strohmaier et al.

(10) Patent No.: US 7,435,863 B2
(45) Date of Patent: *Oct. 14, 2008

(54) HIGH SILICA CHABAZITE, ITS SYNTHESIS AND ITS USE IN THE CONVERSION OF OXYGENATES TO OLEFINS

(75) Inventors: Karl G. Strohmaier, Port Murray, NJ (US); Sebastian C. Reyes, Branchburg, NJ (US); Doron Levin, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 14 days.

This patent is subject to a terminal disclaimer.

(21) Appl. No.: 11/590,230

(22) Filed: Oct. 31, 2006

(65) Prior Publication Data

US 2007/0043251 A1    Feb. 22, 2007

Related U.S. Application Data

(62) Division of application No. 10/370,923, filed on Feb. 20, 2003, now Pat. No. 7,148,172.

(60) Provisional application No. 60/364,450, filed on Mar. 15, 2002.

(51) Int. Cl.
*C07C 1/00* (2006.01)
*C07C 1/20* (2006.01)

(52) U.S. Cl. ............ 585/640; 585/638; 585/639

(58) Field of Classification Search ........ 585/638, 585/639, 640
See application file for complete search history.

(56) References Cited

U.S. PATENT DOCUMENTS

| | | | |
|---|---|---|---|
| 3,030,181 A | | 4/1962 | Milton et al. |
| 4,544,538 A | | 10/1985 | Zones |
| 5,252,527 A | * | 10/1993 | Zones ............ 502/64 |
| 5,554,356 A | | 9/1996 | Saxton et al. |
| 6,187,983 B1 | | 2/2001 | Sun |
| 6,293,999 B1 | | 9/2001 | Cheng et al. |
| 6,296,688 B1 | | 10/2001 | Cheng et al. |
| 7,094,389 B2 | * | 8/2006 | Cao et al. ............ 423/706 |
| 2002/0007101 A1 | * | 1/2002 | Senetar et al. ........ 585/809 |

FOREIGN PATENT DOCUMENTS

| | | |
|---|---|---|
| EP | 453 340 | 10/1991 |
| EP | 453 640 | 10/1991 |
| GB | 868846 | 5/1961 |

OTHER PUBLICATIONS

Delmotte et al., "19F MAS NMR Studies of Crystalline Microporous Solids Synthesized on the Fluoride Medium", *Zoelites*, vol. 10, pp. 778-783 (1990).
Rees et al., "Hydrothermal Reaction of Kaolinite in Presence of Fluoride Ions at pH <10", *Zeolites*, vol. 13, pp. 534-541 (1993).
Yuen et al., "Product Selectivity in Methanol to Hydrocarbon Conversion for Isostructural Compositions of AFI and CHA Molecular Sieves", *Microporous Materials 2*, pp. 105-117 (1994).
Dahl et al., "Structural and Chemical Influences on the MTO Reaction: A Comparison of Chabazite and SAPO-34 as MTO Catalysts", *Microporous and Mesoporous Materials*, vol. 29, pp. 185-190 (1999).
Diaz-Cabanas et al, "Synthesis and Structure of pure SiO2 Polymorph with the Lowest Framework Density", *Chem. Commun.*, pp. 1881 (1998).
Barrer et al., J. Chem. Soc., p. 2822 (1956).

* cited by examiner

*Primary Examiner*—Elizabeth D Wood

(57) ABSTRACT

A porous crystalline material is described having the chabazite framework type and having a composition involving the molar relationship:

$$X_2O_3:(n)YO_2,$$

wherein X is a trivalent element, such as aluminum, boron, iron, indium, and/or gallium; Y is a tetravalent element such as silicon, tin, titanium and/or germanium; and n is greater than 100 and typically greater than 200, such as about 300 to about 4000, for example from about 400 to about 1200. The material is synthesized in a fluoride medium and exhibits activity and selectivity in the conversion of methanol to lower olefins, especially ethylene and propylene.

9 Claims, No Drawings

HIGH SILICA CHABAZITE, ITS SYNTHESIS AND ITS USE IN THE CONVERSION OF OXYGENATES TO OLEFINS

This application is a divisional of U.S. patent application Ser. No. 10/370,923, filed Feb. 20, 2003, now U.S. Pat. No. 7,148,172 which claims priority to U.S. Patent Application No. 60/364,450, filed Mar. 15, 2002, and which are both fully incorporated herein by reference.

CROSS REFERENCE TO RELATED APPLICATIONS

The present application claims the benefit of U.S. Provisional Patent Application Ser. No. 60/364,450, filed Mar. 15, 2002, the disclosure of which is incorporated herein by reference in its entirety.

FIELD

This invention relates to an aluminosilicate form of chabazite having a high silica to alumina molar ratio, its synthesis and its use in the conversion of oxygenates, particularly methanol, to olefins, particularly ethylene and propylene.

BACKGROUND

The conversion of methanol to olefins (MTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, MTO exploits catalytic and micro-architectural properties of acidic molecular sieves under milder temperature conditions to produce high yields of ethylene and propylene from methanol.

Current understanding of the MTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. MTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the MTO reactions. Crystalline microporous materials are the preferred catalysts today because they simultaneously address the acidity and morphological requirements for the reactions. Particularly preferred materials are eight-membered ring aluminosilicates, such as those having the chabazite framework type, and silicoaluminophosphates, such as SAPO-34 and SAPO-18. These molecular sieves have cages that are sufficiently large to accommodate aromatic intermediates while still allowing the diffusional transport of reactants and products into and out of the crystals through regularly interconnected window apertures. By complementing such morphological characteristics with appropriate levels of acid strength and acid density, working catalysts are produced. Extensive research in this area indicates that silicoaluminophosphates are currently more effective MTO catalysts than aluminosilicates. In particular, the control of the silica to alumina molar ratio is a key requirement for the use of aluminosilicates in MTO reactions, since materials with low silica to alumina molar ratios are too acidic and perform poorly. Nevertheless, aluminosilicate zeolites continue to be explored for use in MTO and appear to have yet undiscovered potential.

Chabazite is a naturally occurring zeolite with the approximate formula $Ca_6Al_{12}Si_{24}O_{72}$. Three synthetic forms of chabazite are described in "Zeolite Molecular Sieves", by D. W. Breck, published in 1973 by John Wiley & Sons, the complete disclosure of which is incorporated herein by specific reference. The three synthetic forms reported by Breck are Zeolite "K-G", described in J. Chem. Soc., p. 2822 (1956), Barrer et al; Zeolite D, described in British Patent No. 868,846 (1961); and Zeolite R, described in U.S. Pat. No. 3,030,181 (1962).

U.S. Pat. No. 4,544,538 describes the synthesis of another synthetic form of chabazite, SSZ-13, using N-alkyl-3-quinuclidinol, N,N,N-tri-alkyl-1-adamantammonium cations and/or N,N,N-trialkyl-exoaminonorbornane as a directing agent in a conventional $OH^-$ medium. According to the '538 patent, SSZ-13 typically has a silica to alumina molar ratio of 8 to 50 but higher molar ratios can be obtained by varying the relative ratios of the reactants in the synthesis mixture and/or by treating the zeolite with chelating agents or acids to remove aluminum from the zeolite lattice. However, attempts to synthesize SSZ-13 in $OH^-$ media at silica to alumina molar ratios in excess of 100 have been unsuccessful and have produced ITQ-1 or SSZ-23, depending on the alkali metal cation present. Moreover, increasing the silica to alumina molar ratio of SSZ-13 by dealumination has met with limited success because the small size of the pores makes aluminum extraction difficult and the severity of the treatment may detrimentally affect the crystalline integrity of the material.

Significant work has been conducted on the use of SSZ-13 as a catalyst for MTO reactions. However, investigations to date have shown that the performance of SSZ-13 is always inferior to that of its silicoaluminophosphate analog, SAPO-34. See, for example, Yuen, L.-T., Zones, S. I., Harris, T. V., Gallegos, E. J., and Auroux, A., "Product Selectivity in Methanol to Hydrocarbon Conversion for Isostructural Compositions of AFI and CHA Molecular Sieves", Microporous Materials 2, 105-117 (1994) and Dahl, I. M., Mostad, H., Akporiaye, D., and Wendelbo, R., "Structural and Chemical Influences on the MTO Reaction: A Comparison of Chabazite and SAPO-34 as MTO Catalysts", Microporous and Mesoporous Materials 29, 185-190 (1999).

Recently, a pure silica form of chabazite has been hydrothermally synthesized using N,N,N-trimethyladamantammonium in hydroxide form as the structure-directing agent at nearly neutral pH in the presence of fluoride. See Diaz-Cabanas, M-J, Barrett, P. A., and Camblor, M. A. "Synthesis and Structure of Pure $SiO_2$ Chabazite: the $SiO_2$ Polymorph with the Lowest Framework Density", Chem. Commun. 1881 (1998).

By adding small amounts of aluminum to the synthesis mixture employed by Camblor and his co-workers, the present inventors have for the first time been able to synthesize a pure, highly crystalline aluminosilicate material having the chabazite structure with silica to alumina molar ratios significantly in excess of 100, such as 265. The amount of Al present in such a material is equivalent to only 0.045 Al atom/cage or 1 Al atom per 22 cages. Moreover, the results of this novel synthesis suggest that the Si/Al ratio can be controlled over wide ranges below and above 265.

MTO experiments have now been conducted with this high silica-chabazite at standard conditions of pressure, temperature, and space velocity and show very promising results. The performance of this catalyst is clearly better than any previous results on SSZ-13 and is only slightly inferior to those of the best low acidity SAPO-34 catalysts currently available. Lifetime curves for this catalyst as a function of temperature show fairly typical behavior of MTO catalysts in which an early induction period is followed by a high activity period and the eventual deactivation by coking. Despite the very small amount of aluminum in the catalyst, the activity is quite high, reaching 100% very early in the reaction.

It is to be appreciated that, although the chabazite of the present invention is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

SUMMARY

In one aspect, the invention resides in a porous crystalline material having the structure of chabazite and having a composition involving the molar relationship:

$$X_2O_3:(n)YO_2,$$

wherein X is a trivalent element, such as aluminum, boron, iron, indium, and/or gallium; Y is a tetravalent element such as silicon, tin, titanium and/or germanium; and n is greater than 100 and typically greater than 200, for example from about 300 to about 4000, such as from about 400 to about 1200.

In a further aspect, the invention resides in a method of synthesizing the material of said one aspect of the invention in a fluoride-containing medium.

In still a further aspect, the invention resides in a process for producing olefins comprising the step of contacting an organic oxygenate compound under oxygenate conversion conditions with a catalyst comprising a porous crystalline material having the structure of chabazite and having a composition involving the molar relationship:

$$X_2O_3:(n)YO_2,$$

wherein X is a trivalent element, such as aluminum, boron, iron, indium, and/or gallium; Y is a tetravalent element, such as silicon, tin, titanium and/or germanium; and n is greater than 100.

DETAILED DESCRIPTION OF THE EMBODIMENTS

The present invention relates to a novel form of chabazite and to its manufacture in a fluoride medium. In addition, the invention relates to the use of this novel from of chabazite in a process for the conversion of oxygenates, particularly methanol, to olefins, particularly ethylene and propylene.

In its calcined form, the chabazite of the present invention has an X-ray diffraction pattern having the characteristic lines shown in Table 1 below:

TABLE 1

| d(A) | Relative Intensities (I %) |
|---|---|
| 9.36-8.98 | 80-100 |
| 6.86-6.66 | 20-60 |
| 6.33-6.15 | 0-10 |
| 5.51-5.38 | 5-40 |
| 4.97-4.86 | 5-50 |
| 4.63-4.54 | 0-10 |
| 4.28-4.20 | 20-60 |
| 3.94-3.87 | 0-10 |
| 3.83-3.76 | 0-10 |
| 3.54-3.49 | 5-40 |
| 3.41-3.36 | 5-40 |
| 3.14-3.10 | 0-10 |
| 2.889-2.853 | 5-50 |
| 2.850-2.815 | 5-40 |
| 2.650-2.620 | 0-10 |
| 2.570-2.542 | 0-10 |
| 2.467-2.441 | 0-10 |
| 2.244-2.223 | 0-10 |
| 2.088-2.070 | 0-10 |
| 2.059-2.041 | 0-10 |
| 1.883-1.869 | 0-10 |
| 1.842-1.828 | 0-10 |

These X-ray diffraction data were collected with a Siemens powder X-Ray Diffractometer, equipped with a scintillation detector with graphite monochromator, using copper K-alpha radiation. The diffraction data were recorded by step-scanning at 0.02 degrees of two-theta, where theta is the Bragg angle, and a counting time of 1 second for each step. The interplanar spacing, d's, were calculated in Angstrom units, and the relative intensities of the lines, $I/I_o$ is one-hundredth of the intensity of the strongest line, above background were determined by integrating the peak intensities. It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the framework atom connectivities. These minor effects, including changes in relative intensities, can also occur as a result of differences in cation content, framework composition, nature and degree of pore filling, crystal size and shape, preferred orientation and thermal and/or hydrothermal history.

The chabazite of the present invention has a composition involving the molar relationship:

$$X_2O_3:(n)YO_2,$$

wherein X is a trivalent element, such as aluminum, boron, iron, indium, and/or gallium, typically aluminum; Y is a tetravalent element, such as silicon, tin, titanium and/or germanium, typically silicon; and n is greater than 100 and typically greater than 200, for example from about 300 to about 4000, such as from about 400 to about 1200.

In its as-synthesized form, the chabazite of the present invention has a composition involving the molar relationship:

$$X_2O_3:(n)YO_2:(m)R:(x)F:zH_2O,$$

wherein X, Y and n are as defined in the preceding paragraph and wherein m ranges from about 15 to about 350, such as from about 30 to about 50, z ranges from about 0 to about 10, and x ranges from about 7 to about 175, such as from about 15 to about 25.

The high silica chabazite of the present invention is believed to have a window size that is slightly smaller than that of SAPO-34.

The chabazite of the invention can be prepared from a reaction mixture containing sources of water, an oxide of a trivalent element X, an oxide of a tetravalent element Y, an organic directing agent (R) as described below, and fluoride ions, said reaction mixture having a composition, in terms of mole ratios of oxides, within the following ranges:

| Reactants | Useful | Typical |
|---|---|---|
| $H_2O/YO_2$ | 2-40 | 2-5 |
| $F/YO_2$ | 0.2-1.0 | 0.3-0.7 |
| $R/YO_2$ | 0.2-2.0 | 0.3-1.0 |
| $X_2O_3/YO_2$ | 0.00025-0.02 | 0.0005-0.01 |

The organic directing agent R used herein is conveniently selected from N-alkyl-3-quinuclidinol, N,N,N-tri-alkyl-1-adamantammonium cations, N,N,N-trialkyl-exoaminonorbornane and mixtures thereof and typically is a N,N,N-trimethyl-1-adamantammonium cation.

Crystallization can be carried out at either static or stirred conditions in a suitable reactor vessel, such as for example, polypropylene jars or Teflon®-lined or stainless steel autoclaves, at a temperature of about 100° C. to about 225° C. for a time sufficient for crystallization to occur at the temperature used, e.g., from about 16 hours to about 7 days. Synthesis of the new crystals may be facilitated by the presence of at least 0.01 percent, such as at least 0.10 percent, for example at least 1 percent, seed crystals (based on total weight) of the crystalline product.

After crystallization is complete, the crystals are separated from the mother liquor, washed and calcined to remove the organic directing agent. Calcination is typically conducted at a temperature of about 370° C. to about 925° C. for at least 1 minute and generally not longer than 20 hours. If needed, additional activation of the sieve can be effected, such as by cation exchange or acidification.

As in the case of many catalysts, it may be desirable to incorporate the resultant chabazite with another material resistant to the temperatures and other conditions employed in organic conversion processes. Such materials include catalytically active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a catalytically active material tends to change the conversion and/or selectivity of the catalyst in the oxygenate conversion process. Inactive materials suitably serve as diluents to control the amount of conversion in the process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials.

Naturally occurring clays which can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Other useful binders include inorganic oxides, such as silica, zirconia, titania, magnesia, beryllia, alumina, and mixtures thereof.

In addition to the foregoing materials, the chabazite can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of chabazite and inorganic oxide matrix may vary widely, with the zeolite content ranging from about 1 to about 90 percent by weight and more usually, particularly when the composite is prepared in the form of beads, in the range of about 2 to about 80 weight percent of the composite.

The chabazite of the present invention is particularly suitable for use in a process for converting organic oxygenates to olefins rich in ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms. Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with a diluent, is contacted in the vapor phase in a reaction zone with a catalyst comprising the chabazite of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

The temperature employed in the present process may vary over a wide range. Although not limited to a particular temperature, best results will be obtained if the process is conducted at temperatures in the range of from about 200° C. to about 700° C., such as in the range of from about 250° C. to about 600° C., for example in the range of from about 300° C. to about 550° C. Lower temperatures generally result in lower rates of reaction, and the formation of the desired light olefin products may become markedly slow. However, at higher temperatures, the process may not form an optimum amount of light olefin products, and the coking rate may become too high.

Light olefin products will form, although not necessarily in optimum amounts, at a wide range of pressures, including but not limited to autogeneous pressures and pressures in the range of from about 0.1 kPa to about 100 MPa. Conveniently, the pressure is in the range of from about 6.9 kPa to about 34 MPa, such as in the range of from about 48 kPa to about 0.34 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$. One or more diluents may be fed to the reaction zone with the oxygenates, such that the total feed mixture comprises diluent in a range of from about 1 mol % to about 99 mol %. Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Typical diluents are water and nitrogen.

A practical embodiment of a reactor system for the present process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

The invention will now be more particularly described with reference to the following Examples.

EXAMPLE 1

An aluminosilicate reaction mixture was prepared by stirring a mixture of 37.5 g of 0.823M ROH (R=N,N,N-trimethyladamantammonium) solution and 0.094 g of $Al(NO_3)_3 \cdot 9H_2O$ with 13.0 g of TEOS (tetraethylorthosilicate) in a tared plastic beaker for three days until the weight of the formed gel was reduced to 12.7 g. The gel was then ground to a powder with mortar and pestle and placed into a 125 ml teflon-lined autoclave. Then 1.6 g of 49% HF aqueous solution was stirred in. The resultant mixture had the following molar composition:

$$0.6\ HF : 0.5\ ROH : 0.002\ Al_2O_3 : SiO_2 : 3.7 H_2O$$

The mixture was crystallized in an autoclave at 150° C. for 65 hours on the shelf of a tumbling oven at 20 rpm. After cooling, the mixture was filtered, washed with water, and dried to constant weight to give 4 g of a white solid. The resultant product was then calcined at 650° C. for 3 hours. The calcined product had the X-ray diffraction pattern of Table 2 demonstrating the material has the chabazite framework type. Analysis of the product showed the silica/alumina molar ratio to be 530. $^{27}Al$ NMR confirmed that the aluminum was in the zeolite framework.

TABLE 2

| 2-Theta | d(A) | Relative Intensities (I %) |
|---|---|---|
| 9.646 | 9.1611 | 100.0 |
| 13.089 | 6.7584 | 30.8 |
| 14.187 | 6.2375 | 4.8 |
| 16.274 | 5.4420 | 16.5 |
| 18.037 | 4.9140 | 22.3 |
| 19.346 | 4.5842 | 2.7 |
| 20.943 | 4.2383 | 37.6 |
| 22.346 | 3.9751 | 1.8 |
| 22.771 | 3.9020 | 2.2 |
| 23.427 | 3.7941 | 2.4 |
| 25.321 | 3.5145 | 17.8 |
| 26.345 | 3.3802 | 10.0 |
| 28.115 | 3.1712 | 1.9 |
| 28.600 | 3.1186 | 2.6 |
| 30.038 | 2.9724 | 1.2 |
| 31.129 | 2.8707 | 25.2 |
| 31.564 | 2.8322 | 11.3 |
| 32.889 | 2.7210 | 1.2 |
| 34.000 | 2.6346 | 2.1 |
| 35.083 | 2.5557 | 4.4 |
| 36.582 | 2.4543 | 4.5 |
| 39.270 | 2.2923 | 1.3 |
| 40.353 | 2.2332 | 3.4 |
| 43.487 | 2.0793 | 4.1 |
| 44.148 | 2.0497 | 2.7 |
| 48.482 | 1.8761 | 2.6 |
| 49.644 | 1.8349 | 3.6 |

EXAMPLE 2

The calcined product from Example 1 was used to conduct a series of MTO experiments in which methanol was contacted with the catalyst at a WHSV of 100 $h^{-1}$, a pressure of 40 psia (274 kPa) and various temperatures from 400-500° C. Tables 3 and 4 summarize the product distribution for the experiments. Table 3 summarizes the results at 100 WHSV and shows high prime olefin yields, high ethylene/propylene ratios, and low propane yield. In particular, the ethylene/propylene ratios are significantly higher than those normally obtained with SAPO-34 catalysts. The performance of the catalyst improves with temperature both in terms of product selectivity as well as in lifetime.

TABLE 3

| Temperature | 400° C. | 438° C. | 475° C. | 500° C. |
|---|---|---|---|---|
| Gms MeOH converted at 10% MeOH conversion | 3.68 | 5.83 | 9.20 | 12.32 |
| $CH_4$ | 2.88 | 2.56 | 3.01 | 3.28 |
| $C_2=$ | 31.07 | 32.75 | 35.81 | 37.61 |

TABLE 3-continued

| Temperature | 400° C. | 438° C. | 475° C. | 500° C. |
|---|---|---|---|---|
| $C_2$ | 0.23 | 0.33 | 0.41 | 0.44 |
| $C_3=$ | 38.80 | 38.03 | 36.94 | 36.04 |
| $C_3$ | 1.19 | 1.19 | 0.74 | 0.53 |
| $C_4+$ | 22.24 | 21.88 | 19.46 | 18.28 |
| $C_2= + C_3=$ | 69.87 | 70.78 | 72.75 | 73.65 |
| $C_2=/C_3=$ | 0.80 | 0.86 | 0.97 | 1.04 |

Table 4 lists average selectivities of the butene isomers as a function of temperature. The most abundant isomer is trans-2-butene, followed by much smaller amounts of 1-butene and cis-2-butene. In particular, the ratio of trans-2-butene to cis-2-butene and the ratio of trans-2-butene to 1-butene are significantly higher than those normally obtained with SAPO-34 catalysts.

TABLE 4

| Temperature | 1-C4= | t-2-C4= | c-2-C4= |
|---|---|---|---|
| 400 | 4.00 | 12.22 | 1.58 |
| 438 | 4.77 | 11.05 | 2.14 |
| 475 | 4.61 | 9.59 | 2.04 |
| 500 | 4.46 | 9.19 | 1.95 |

The preceding Examples suggest that aluminosilicates of similar or superior performance than silicoaluminophosphates in MTO reactions are possible by tailoring acidity and window sizes to optimal levels. The materials of the present invention combine very sparsely distributed strong acid sites with a very precise control of 8-ring window size to deliver high yields of ethylene and propylene. It is believed that the performance of these catalysts can be further improved by changes in acid site density (i.e., Si/Al ratio), acid strength (e.g., use of Ga instead of Al), and crystal size. Temperature, in particular, is a very important optimization variable because, in addition to the standard Arrhenius dependence of the reactions, the diffusion processes are activated, and the unit cell size changes. The present catalysts should also have better hydrothermal stability and be easier to regenerate than aluminosilicates with higher acidity (lower Si/Al ratios) and/or silicoaluminophosphates typically used in MTO processes.

What is claimed is:

1. A process for producing olefins comprising the step of contacting an organic oxygenate compound under oxygenate conversion conditions with a catalyst comprising a porous crystalline material having the structure of chabazite and having a composition, as synthesized, involving the molar relationship:

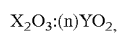

wherein X is a trivalent element, Y is a tetravalent, and n is from greater than 100 to about 4000.

2. The process of claim 1 wherein n is greater than 200.

3. The process of claim 1 wherein n is from about 150 to about 2000.

4. The process claim 1 wherein n is from about 200 to about 600.

5. The process of claim 1 wherein X comprises aluminum and Y comprises silicon.

6. The process of claim 1 wherein said organic oxygenate compound is selected from methanol, dimethyl ether, and mixtures thereof.

7. The process of claim 1 wherein said organic oxygenate compound comprises methanol, dimethyl ether, and mixtures thereof.

8. The process of claim 1, wherein X is selected from aluminum, boron, indium, and/or gallium, and wherein Y is selected from silicon, tin, titanium, and/or germanium.

9. The process of claim 1, wherein the porous crystalline material, as synthesized, consists essentially of an oxide of trivalent element X and an oxide of tetravalent element Y.

* * * * *